US009181519B2

(12) United States Patent
Michiels

(10) Patent No.: US 9,181,519 B2
(45) Date of Patent: Nov. 10, 2015

(54) BIOREACTOR

(75) Inventor: Mark Michiels, Antwerp (BE)

(73) Assignee: Proviron Holding, Hemiksem (BE)

( * ) Notice: Subject to any disclaimer, the term of this patent is extended or adjusted under 35 U.S.C. 154(b) by 1021 days.

(21) Appl. No.: 12/679,632

(22) PCT Filed: Sep. 24, 2008

(86) PCT No.: PCT/EP2008/062801
§ 371 (c)(1),
(2), (4) Date: Mar. 23, 2010

(87) PCT Pub. No.: WO2009/040383
PCT Pub. Date: Apr. 2, 2009

(65) Prior Publication Data
US 2010/0285575 A1    Nov. 11, 2010

(30) Foreign Application Priority Data

Sep. 24, 2007  (BE) .................................. 2007/0454
Dec. 21, 2007  (EP) .................................. 07124035

(51) Int. Cl.
*C12M 1/00*    (2006.01)
*C12M 1/12*    (2006.01)

(52) U.S. Cl.
CPC .............. *C12M 23/26* (2013.01); *C12M 21/02* (2013.01); *C12M 23/06* (2013.01); *C12M 29/14* (2013.01)

(58) Field of Classification Search
CPC ...... C12M 21/02; C12M 29/14; C12M 23/26; C12M 23/06; C12M 23/14; C12M 23/28; C12M 33/00; C12M 23/22; C12M 29/00; C12M 41/44

USPC .............. 435/289.1, 292.1, 383, 296.1, 304.1
See application file for complete search history.

(56) References Cited

U.S. PATENT DOCUMENTS

| 3,955,317 A * | 5/1976 | Gudin ........................... 435/420 |
| 5,068,195 A | 11/1991 | Howell et al. |
| 5,171,683 A * | 12/1992 | Kertz ............................ 435/430 |
| 5,534,417 A * | 7/1996 | Arad et al. ....................... 435/67 |
| 5,543,417 A | 8/1996 | Waldstreicher |
| 6,391,638 B1 * | 5/2002 | Shaaltiel ....................... 435/383 |
| 2006/0131765 A1 * | 6/2006 | Terentiev et al. ............... 261/93 |
| 2008/0160591 A1 * | 7/2008 | Willson et al. ................ 435/132 |

FOREIGN PATENT DOCUMENTS

| EP | 0 258 795 A2 | 3/1988 |
| EP | 0 471 947 A1 | 2/1992 |
| EP | 0 725 134 A2 | 8/1996 |
| WO | 2008/079724 A2 | 7/2008 |

* cited by examiner

*Primary Examiner* — William H Beisner
*Assistant Examiner* — Danielle Henkel
(74) *Attorney, Agent, or Firm* — Sughrue Mion, PLLC

(57) ABSTRACT

The invention relates to a bioreactor which comprises a closed housing with a housing wall and at least one chamber which is connected to the housing wall. The at least one chamber comprises a chamber inlet and outlet for respectively supplying and discharging material to and from the at least one chamber. The housing comprises a housing inlet for supplying material to the chamber inlet and a housing outlet for discharging treated material from the chamber outlet to the outside of the bioreactor. The bioreactor forms a closed volume in which a reactor pressure prevails in the bioreactor which is higher than the external pressure outside the bioreactor, in such a way that the bioreactor is self-supporting.

16 Claims, 7 Drawing Sheets

BIOREACTOR

This invention relates to a bioreactor comprising at least one chamber with a chamber wall, the at least one chamber being provided for receiving biomass, the bioreactor further comprising a chamber inlet for supplying the material to be treated to the at least one chamber and a chamber outlet for discharging treated material from the at least one chamber, the at least one chamber being made of a material that comprises at least one film of a flexible plastic material, as described in the preamble of the first claim.

Within the framework of an expected deficit of fossil fuels in the future, it has been decided that in 2010 5.75% of the fuels have to be of biological origin. In 2020, 20% of the fuels have to consist of biofuel. The increasing demand for biofuels creates an increasing demand for biomass, because biofuel consists of or is derived from biomass. Biomass can be obtained from domestic waste, sludge, wood waste, industrial waste streams, water treatment installations, . . . . However, in order to be able to have a sufficiently large amount of biomass for energy production, additional biomass is grown on agricultural land, specifically for use in energy production. The growth of crops is a relatively slow process and requires large amounts of agricultural land. There is therefore a need for an efficient method for growing biomass with an increased production capacity.

U.S. Pat. No. 5,534,417 describes a bioreactor which is capable of growing micro-organisms on industrial scale at low cost. The reactor known from U.S. Pat. No. 5,534,417 comprises a plurality of elongated cells of a flexible polyethylene, which are capable of receiving a biomass. The cells are suspended in vertical position to a supporting structure. The cells are produced by locally connecting two polyethylene foils in height direction, whereas the space between the foils defining the cells. If desired, a plurality of these rows of cells can be provided. The bioreactor further comprises:
  a gas inlet and outlet for bubbling the gas and ventilating each cell
  at least one inlet and/or outlet for supplying nutrients for the biomass and remove biomass
  a manifold, which is connected to all outlets, to receive biomass from and to transport biomass out of the bioreactor.
In order to minimize interference of light penetration between the cells, the distance between two adjacent cells is equal to or smaller than 100 mm.

EP-A-0725134 describes a flexible bioreactor consisting of two compartments being separated by a semi-permeable membrane. Cells are stored in a first, small compartment, defined by a semi-permeable membrane and an outer gas permeable wall, while medium is stored in a second, large compartment, which is defined by the semi-permeable membrane and a second outer wall of the bioreactor. The gas permeable membrane of the cell compartment allows for direct gas exchange for the cells over a short diffusion path.

EP-A-0471947 describes a culture bag which comprises a culture room for culturing cells. The culture bag is made of plastic sheet having good flexibility, clarity and gas permeability and is formed by fusion-bonding the plastic sheet. The culture bag comprises at least one opening which is at least used to inject and discharge a medium, to inject cells and to recover cultured cells.

Bioreactors known from U.S. Pat. No. 5,543,417, EP-A-0725134 and EP-A-0471947 have the disadvantage that the reactor cells in which the cells are cultured have to be suspended to an additional supporting structure. This limits the application possibilities of the bioreactor and makes the installation complicated and expensive. Another disadvantage is that, when setting up the bioreactor, each of the cells needs to be separately connected to a central inlet and outlet.

WO-A-2008/079724 describes a photobioreactor which comprises at least one chamber provided for receiving biomass. The at least one chamber comprises a flexible, transparent plastic or composite film. The at least one chamber is surrounded by a water basin, which provides the photobioreactor with structural support. The at least one chamber comprises a chamber inlet and outlet for supplying the material to be treated to the at least one chamber, respectively discharging treated material from the at least one chamber. The photobioreactor known from WO-A-2008/079724 has the disadvantage that, in order to set up the photobioreactor, the at least one chamber needs to be connected to the water basin. Another disadvantage is that, when setting up the photobioreactor, each of the chamber inlets/outlets needs to be separately connected to a central inlet and outlet, which makes the installation cumbersome and expensive.

It is an objective of this invention to provide a bioreactor which can be placed and set up in a simplified way such that a working bioreactor is obtained.

This is achieved according to the invention with a bioreactor which shows the technical properties of the first claim.

Thereto the bioreactor of this invention is characterized in that
  the bioreactor forms a closed volume in which the at least one chamber is included
  in that the bioreactor comprises a closed housing with a housing wall, the at least one chamber being connected to the housing wall, the housing comprising a housing inlet which is connected to the chamber inlet for supplying material to the chamber inlet and a housing outlet which is connected to the chamber outlet for discharging treated material from the chamber outlet
  in that in the bioreactor a reactor pressure is maintained which is higher than the external pressure outside the bioreactor, in such a way that the bioreactor is self-supporting.

The bioreactor according to this invention comprises a closed volume. Because the pressure inside the closed volume of the bioreactor is higher than the surrounding pressure outside the bioreactor, the bioreactor is self-supporting, notwithstanding the bioreactor is made of a flexible foil. Because of this self-supporting property it is not necessary to connect or suspend the bioreactor to an external rigid supporting structure of for instance a metal rack or to provide a rigid supporting structure in the bioreactor to set up the bioreactor. In the bioreactor of this invention the housing and chamber inlet and the housing and chamber outlet are already connected, as a result of which the connections need not to be established upon erection of the bioreactor. This results in a decrease of the overall set up time of the bioreactor and in a decrease of the amount of material needed for the overall system. As a result of this, a decrease of both the installation cost and material cost can be obtained.

The bioreactor according to this invention further comprises a closed housing with a housing wall and at least one chamber which is connected to and integrated within the housing wall. Because of this integrated structure, the chambers do not need to be separately connected to the housing when setting up the bioreactor. The presence of a housing offers an additional protection of the chambers which contain the biomass. It decreases the risks to the occurrence of leaks in the wall of the chambers because of for example bad weather conditions. The at least one chamber does not need to be connected from top to bottom to the housing wall. It is sufficient that the at least one chamber is at least partly connected to the housing wall, for instance only with a lower end.

The at least one chamber comprises a chamber inlet for supplying the material to be treated to the at least one chamber and a chamber outlet for discharging treated material from the at least one chamber. The housing, to which the at least one chamber is connected to, comprises a housing inlet connected to the chamber inlet for supplying material to the chamber inlet of the at least one chamber and a housing outlet connected to the chamber outlet for discharging treated material from the chamber outlet to the outside of the bioreactor.

The combination of all these aspects have the advantage that setting up of the bioreactor according to this invention is extremely simple, in particular it is done by ensuring that in the interior of the bioreactor an overpressure prevails as compared to the surrounding pressure. This can for instance be achieved by filling at least a part of the inside of the bioreactor with a gas and/or a fluid under pressure. Demounting of the bioreactor can also be done in a very easy way: by releasing the overpressure the structure of the bioreactor collapses and then the bioreactor can be rolled up or folded up. This self-supporting property does not only results in a substantial decrease of the installation costs, but also in a reduced reactor cost as such because there is no need for using an expensive and complicated supporting structure. The bioreactor according to this invention further presents the advantage that the volume being taken by the material when it is not in use or when it is stored, is minimal. The bioreactor made of flexible sheet material can in fact be stored in folded up or rolled up condition and can be sterilized when needed. This also results in a substantially simplified and cheaper transport. Because the bioreactor according to this invention does not require to mount the individual chambers to an external structure, nor to establish the individual connections between the chamber and housing inlet and chamber and housing outlet, the risk to the occurrence of contamination within the bioreactor is minimized.

In the bioreactor according to this invention the at least one chamber preferably extends in height direction of the bioreactor. When using the bioreactor as photobioreactor with the aim of, for example, growing algae, the yield of the reactor is increased in case the chambers extend in height direction. A close stacking of chambers which extend in height direction of the bioreactor is preferred, because it results in a higher biomass efficiency.

Preferably, the housing inlet and outlet and chamber inlet and outlet are made in one piece with the bioreactor. This has the advantage that the at least one chamber does not need to be separately connected to a supply and discharge pipe. To provide the at least one chamber with material to be treated and to discharge the treated material from the bioreactor, it is sufficient to connect the bioreactor with respectively its housing inlet and outlet to respectively the supply and discharge pipe. Such a construction has the advantage that because the at least one chamber and the chamber and housing inlets and outlets are integrated in the bioreactor, the bioreactor is set up in one simple step, without the need to separately connect the individual chambers to an external structure or supply or discharge pipe.

Preferably, the at least one chamber inlet and outlet are made of a first flexible sheet material in one piece with the bioreactor. This construction has the advantage that the manufacturing of the entire bioreactor can be simplified and automated. Preferably, the at least one housing inlet and outlet are made of a second flexible sheet material in one piece with the bioreactor. This construction has the advantage that the manufacturing of the entire bioreactor can be simplified and automated. Preferably, both the chamber inlet and outlet and the housing inlet and outlet are made of a flexible sheet material. The first and the second flexible sheet material can be the same or they may differ. The first and the second flexible sheet material of respectively the chamber inlet/outlet and the housing inlet/outlet can be the same or differ from the flexible sheet material in which the rest of the bioreactor is made. The construction of the bioreactor in a flexible material, comprising one or more different flexible sheet materials, offers the additional advantage that the system can be recycled in a very easy way. Another advantage is that the bioreactor can be sterilized in a very easy way. As with other systems all different parts of the bioreactor need to be treated separately, the bioreactor according to this invention can be sterilized as a whole. In fact, this sterilization process can be done during fabrication of the bioreactor. No additional sterilization is required on site. This is due to the fact that because the bioreactor forms a closed volume and does not need to be connected to an external structure, the risk to contamination during set-up is minimized.

Because the bioreactor as a whole can be made of a flexible plastic foil and no external structure is needed to which the chambers need to be connected, a larger freedom is left regarding the locations where the bioreactor can be set up. It is for instance possible to use the bioreactor on/under the sea. The bioreactor can for instance be used on locations where it is not possible or dangerous for ships to sail, for instance in the neighborhood of wind turbine parks. The bioreactor can in other words be used in places which actually cannot be used.

The at least one chamber preferably comprises a first and a second wall which form a surrounding wall of the chamber, the first and second wall being at least partly connected to each other in height direction of the chamber and the first and second wall being made of a flexible sheet of plastic material. A further material reduction and a further simplification of the construction is provided in case the first and/or second wall of the chamber forms part of the surrounding wall of the bioreactor.

In a first preferred embodiment of the chamber, the first and second wall of the chamber respectively comprises a first and second upper edge and a first and second lower edge, the first and second upper edges being connected to each other and the first and second lower edge being connected to each other, in such a way that a chamber with a closed volume is provided. An example of such a bioreactor is a reactor with the form of a honeycomb structure.

In a second preferred embodiment of the chamber the first and second wall of the chamber respectively comprises a first and second upper edge and a first and second lower edge, and the housing of the bioreactor comprises an upper and lower edge, and the housing of the bioreactor comprises an upper and lower wall and a surrounding wall. The first and second upper edge are connected to the upper wall of the housing and the first and second lower edge are connected with the lower wall of the housing, and an upstanding edge of the chamber adjacent to the surrounding wall of the housing is connected to this surrounding wall over at least part of its height. In this embodiment a chamber with a closed volume is provided because the upper and lower wall of the chamber is formed by the upper and lower wall of the housing.

This connection can be obtained through any method known by the person skilled in the art, for instance by welding or gluing or any other way ought suitable by the person skilled in the art, and leaves the possibility to adjust the dimensions of the chambers to the aimed application.

The increased pressure in the bioreactor can be obtained in different ways. According to a first embodiment, an increased pressure is maintained in the at least one chamber, in such a way that the pressure in the chamber is higher than the pressure outside the bioreactor. According to a second embodiment, an increased pressure is maintained because the bioreactor comprises a plurality of rows of adjacent chambers, a space being provided between adjacent rows of chambers for receiving a medium under pressure which is higher than the pressure outside the bioreactor, but lower than the pressure in the at least one chamber.

The means for maintaining the increased pressure can be means which are known to the person skilled in the art, such as for instance a fluid or a gas or a two- or more layer system with a lower and an upper layer, the lower layer being a first fluid and the upper layer being chosen from a second fluid or a gas.

The invention is further elucidated in the attached figures and figure description.

Figure 1:
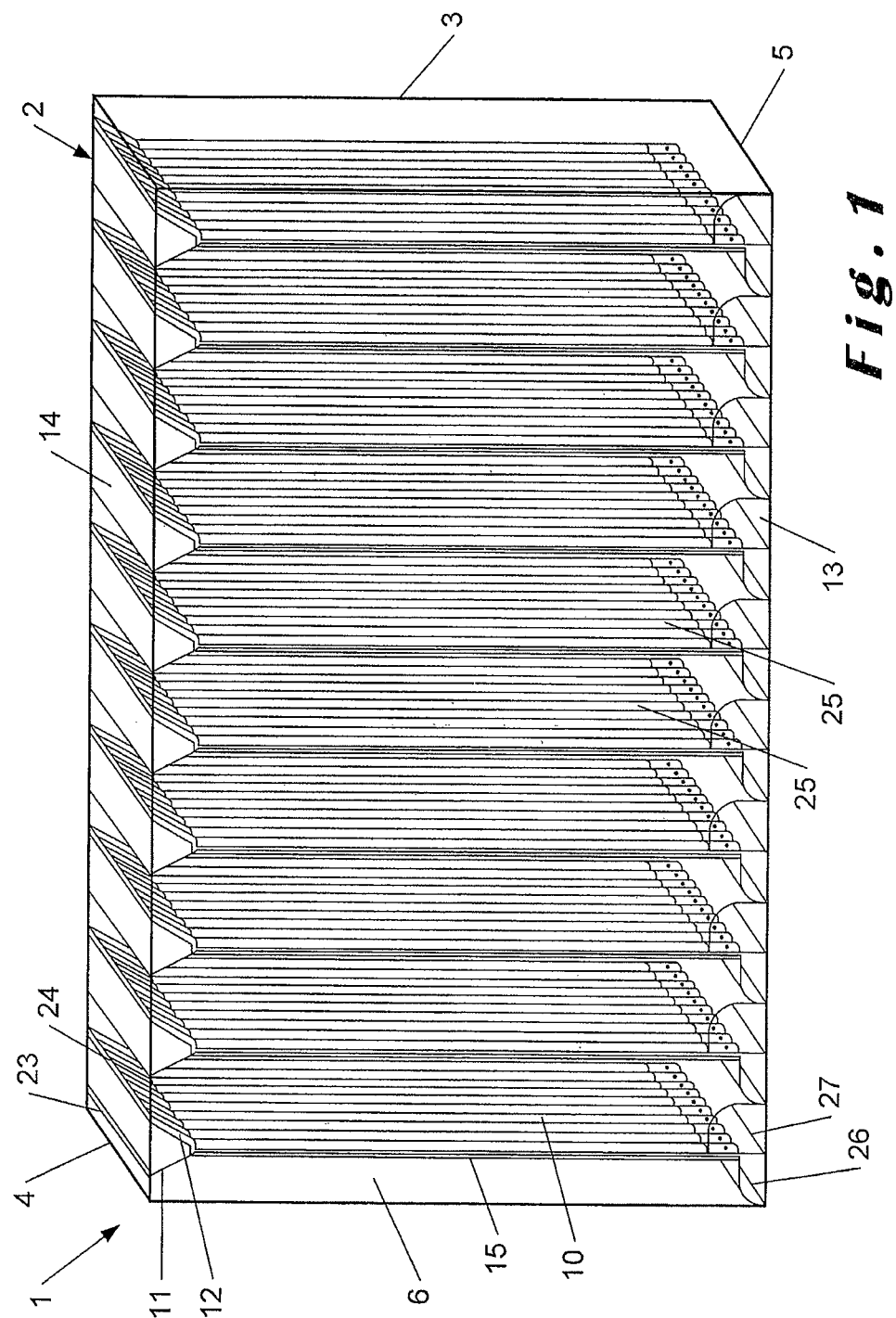
FIG. 1 shows a view in perspective of the inside of a preferred embodiment of the bioreactor according to this invention.

A first preferred embodiment of the bioreactor 1 according to this invention is shown in FIG. 1 and comprises a closed housing 2 with a wall which encloses a closed inside 6. The housing wall comprises a surrounding wall 3 and an upper and a lower wall 4, 5. The bioreactor also comprises at least one and preferably a plurality of chambers 10 which are at least partly connected to the wall of the housing 2.

The wall of the housing is made of a sheet of a flexible plastic material. Thereto, any plastic material known to the person skilled in the art can be used, for instance polyethylene, PVC, polypropylene, nylon or a multilayer construction comprising one or more layers of these materials. The surrounding wall, upper and lower wall of the housing can be made of the same or different materials. In case the bioreactor is used as a photobioreactor, the flexible plastic material is preferably transparent to light. In order to obtain a higher light intensity in the inside of the bioreactor in order to increase the biomass production in case of close stacking of the chambers, the lower wall is preferably made of a plastic material which reflects the light, in particular in case the bioreactor is used as a photobioreactor.

In a preferred embodiment, an additional material provided for controlling the temperature inside the bioreactor, is added to the housing wall material or provided in the form of an additional layer on top of at least part of the housing wall. This is in particular suitable in case the bioreactor is used as a photobioreactor. The material can be any material considered suitable by the person skilled in the art, such as for instance copper sulphate. By adding for instance an additional layer of copper sulphate on top of the upper housing wall of the bioreactor, certain frequencies of the light will be absorbed in the additional layer and will be blocked from entering the bioreactor. The absorption may result in a better control of the temperature inside the bioreactor, as a result of which the efficiency of the bioreactor can be increased.

The inside 6 of the bioreactor comprises at least one chamber 10, in which the material to be treated is reacted or transformed or treated to form an end product. The chamber 10 preferably extends in height direction of the bioreactor.

The bioreactor according to this invention preferably comprises a row 25 of adjacent chambers or a plurality of such rows. The rows can extend in transversal or longitudinal direction of the bioreactor and increase the reactor surface and volume. Preferably a plurality of such rows 25 are provided in the inside 6 of the housing. Adjacent rows preferably extend parallel to each other and to one of the side walls of the bioreactor, although this is not necessary.

Figure 8:
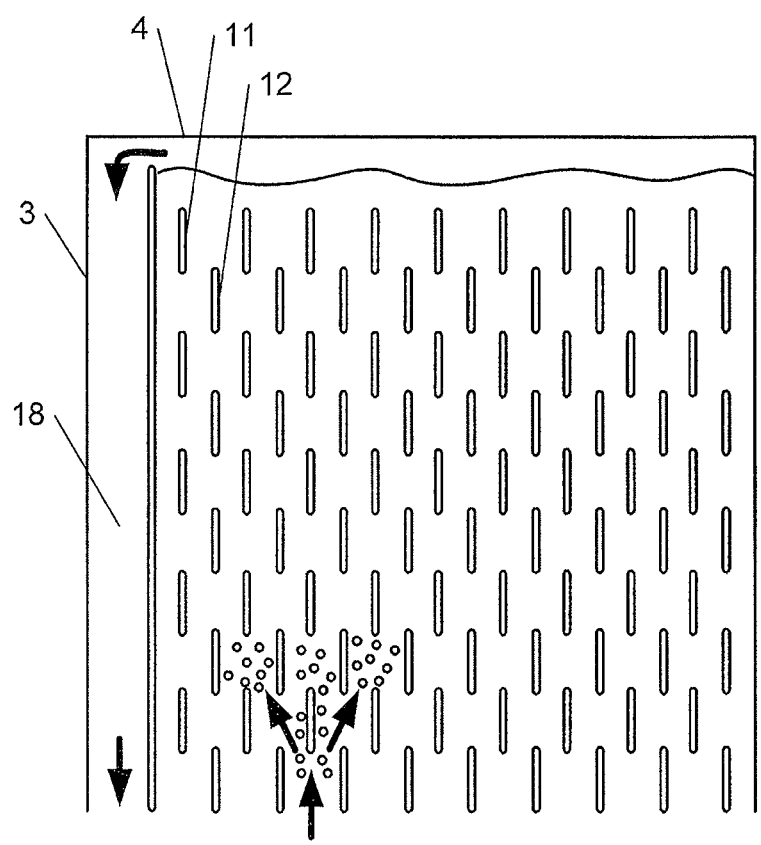
FIG. 8 shows a detail of another preferred embodiment of the bioreactor according to the present invention.

Each chamber comprises a surrounding wall 15, which comprises a first and second opposing chamber wall 11, 12. The first chamber wall 11 is preferably made of a first plastic foil, the second chamber wall 12 is preferably made of a second plastic foil as is shown in FIG. 1. The first and second plastic foil are locally connected to each other. A plurality of adjacent chambers is obtained by connecting the first and second foil to each other over at least a part of their height as is for instance shown in FIG. 1. The connection can be done by any method known to the person skilled in the art, for instance by welding or gluing or any other connection technique. The connection can be continuous in case flow between adjacent chambers is undesired as is shown in FIG. 1, or interrupted in case the possibility for controlling and diverging the liquid and gas flow throughout one or several chambers is desired. Interrupting the connection has the advantage that a large exchange of materials between the different chambers is obtained. In case the bioreactor is for instance used as a photobioreactor, wherein gas and material to be treated are delivered to a chamber, the gas bells will have a large range and will be directed to several chambers and pass continuously to a number of adjacent chambers. The gas bells as well as the material flow will be slowed down by the interruptions between the different chambers, which results in a prolonged contact and a better gas exchange with the material to be treated. As a result the efficiency of the bioreactor will be improved. Preferably, the positions of the joints are positioned staggered with respect to each other as is shown in FIG. 8. Such a construction is preferred, since it results in a more homogeneous partition of the gas bells and the material to be treated between the different chambers and in a better blending. Another advantage of the interrupted connection is that the bioreactor does not need to be completely filled in order to achieve exchange between adjacent chambers. The interruption provides in a continuous exchange, independent of the amount of material with which the bioreactor is filled. Another advantage of this continuous exchange is that the bioreactor is less dependent from level deviations of the surface on which the bioreactor is placed.

Figure 4:
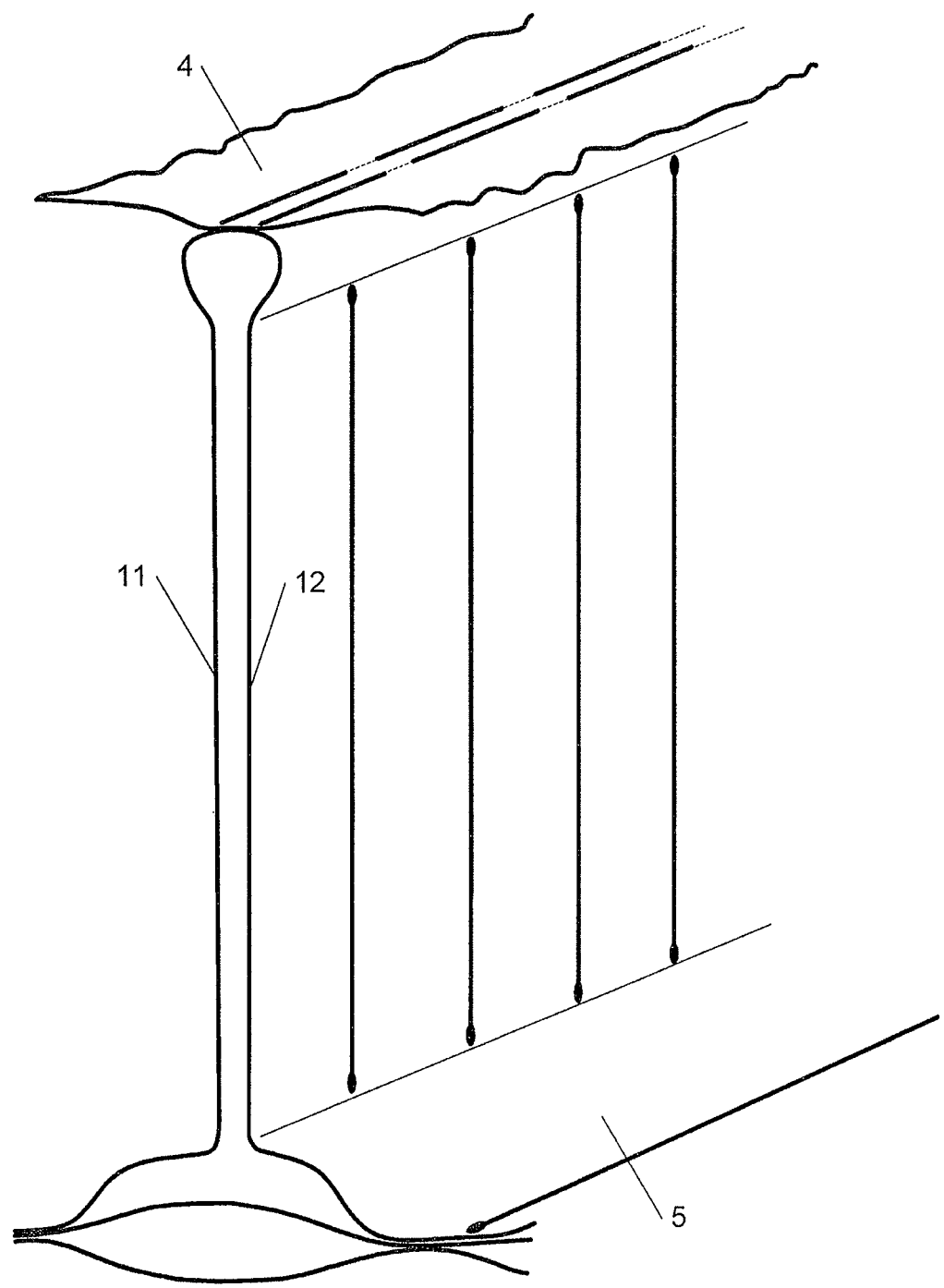
FIG. 4 shows a detail of a further preferred embodiment of adjacent chambers of the bioreactor according to this invention.

The first and second foil can be made of the same or different material, but are preferably made of the same material. The first and second chamber wall may alternatively be made of one foil as is shown in FIG. 4. By locally connecting parts of the foil, a number of adjacent chambers is created, as shown in FIG. 4. The connection can be continuous or interrupted. Preferably, the at least one chamber is made of a materials which is transparent for light, especially when the bioreactor is used as a photobioreactor. This material can be the same or different material as the one of the housing wall.

The connection of the first and second foil permits adjustment of the dimensions of the chambers 10 to the aimed application. It is for instance possible that the distance between consecutive connections is constant, resulting in a bioreactor in which all chambers have one and the same volume. It is however also possible to vary the distance between consecutive connections and to provide a bioreactor with chambers with different volumes.

At least part of the chambers 10, but preferably all chambers 10, are connected to the wall of the housing, making it possible that the housing 2 of the bioreactor, together with the chambers 10 which function as reactor volume, are set up in one time as one whole, without the need to connect the chambers to the housing in a separate step. According to the invention, this can be achieved in a number of different ways.

Figure 3:
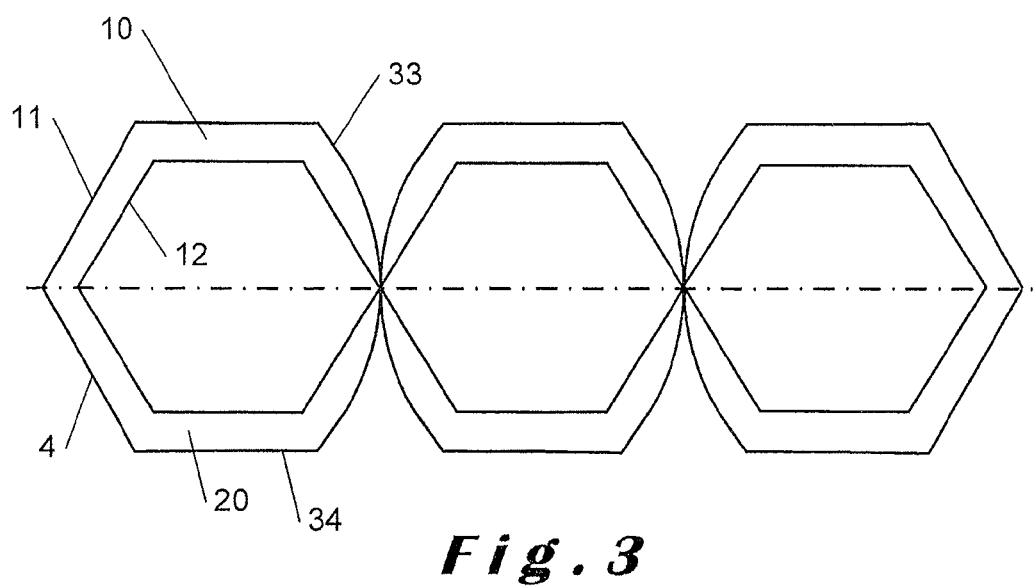
FIG. 3 shows a horizontal cross section of another preferred embodiment of adjacent chambers of the bioreactor according to this invention.

According to a first embodiment shown in FIG. 3, the first or the second wall 11, 12 of the chamber 10 forms part of the surrounding wall of the housing of the bioreactor. In particular, a side 33 of the surrounding wall is formed by the sheet which forms the wall of the chambers 10 lying at that side. The other side 34 of the surrounding wall is formed by the sheet which forms the wall of the chambers 20 lying at the other side. In this embodiment the first wall 11 of the chamber 10, 20 comprises a first upper edge and a first lower edge and the second wall 12 of the chamber 10, 20 comprises a second upper edge and a second lower edge. The first and second upper edge are connected to each other and the first and second lower edge are connected to each other, in such a way that closed chambers 10, 20 are provided. Such a bioreactor is very easy in construction and can be installed in a few operations. The bioreactor preferably has the form of a honeycomb structure as shown in FIG. 3, but can take any other form known to the person skilled in the art, as long as the bioreactor is self-supporting.

Figure 2:
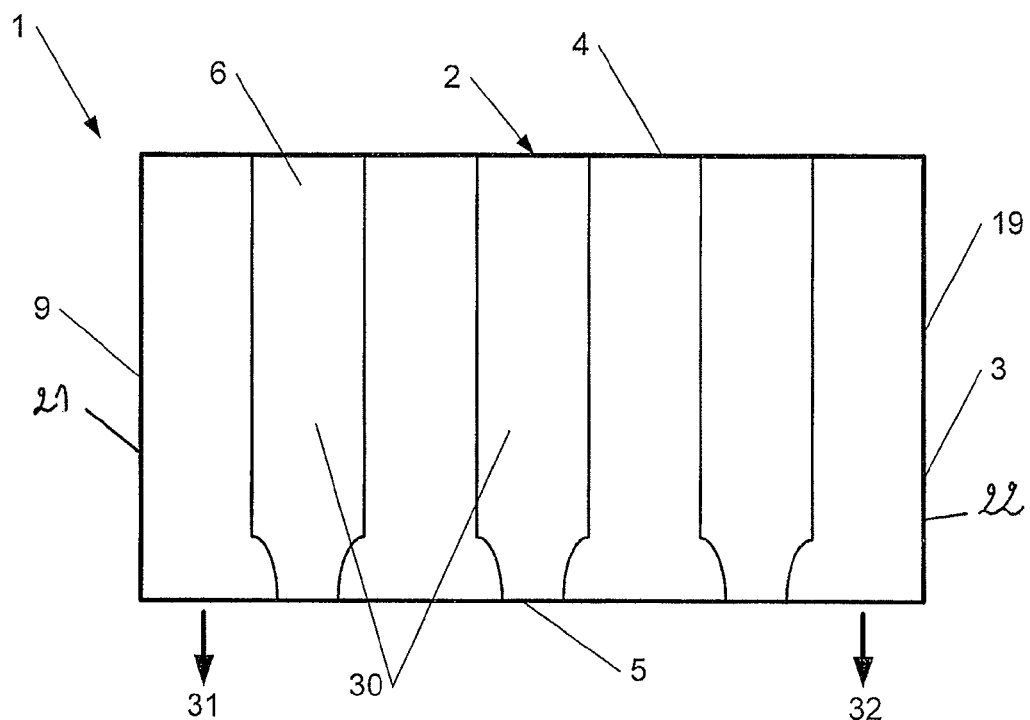
FIG. 2 shows a detail of a preferred embodiment of adjacent chambers of the bioreactor according to this invention.

According to a second preferred embodiment shown in FIG. 1, a plurality of rows 25 of adjacent chambers 10 is provided in the inside 6 of the housing 2. In the shown embodiments, the rows extend in transversal direction of the reactor, but the rows can also extend in longitudinal direction of the reactor or in any other direction. The rows of chambers are connected to the housing. Thereto, the first foil comprises a first upper edge 23 and the second foil comprises a second upper edge 24. The first and second upper edge 23, 24 are connected to the upper wall 4 of the housing, preferably by means of a continuous connection. The first sheet comprises a first lower edge 26, the second sheet comprises a second lower edge 27. The first and second lower edge 26, 27 are connected to the lower wall 5 of the housing by means of a continuous connection. If desired, the first wall 21 of the first row of chambers 31 can form a first side wall of the housing and can thus be integrated in the first side wall 9 of the housing 2 as is shown in FIG. 2, and the second wall 22 of the last row of chambers 32 can form a second side wall 19 of the housing and can thus be integrated in the side wall of the housing. The first and second side wall 9, 19 are hereby located at opposite side of the housing 2. This embodiment results in material saving. As shown in FIG. 2, a space 30 is provided between adjacent rows of chambers 10, 20.

If desired, a detachable connection of the chambers of the housing can be provided in such a way that one or more rows of chambers can be exchanged if needed.

According to a third embodiment shown in FIG. 4, the first and second wall 11, 12 of the chamber or row of chambers is formed by one sheet, which is alternately connected to the upper wall 4 and the lower wall 5 of the housing 2. The connection is preferably continuous, but can also be interrupted, in case flow to the spaces 30 is aimed at.

Figure 5:
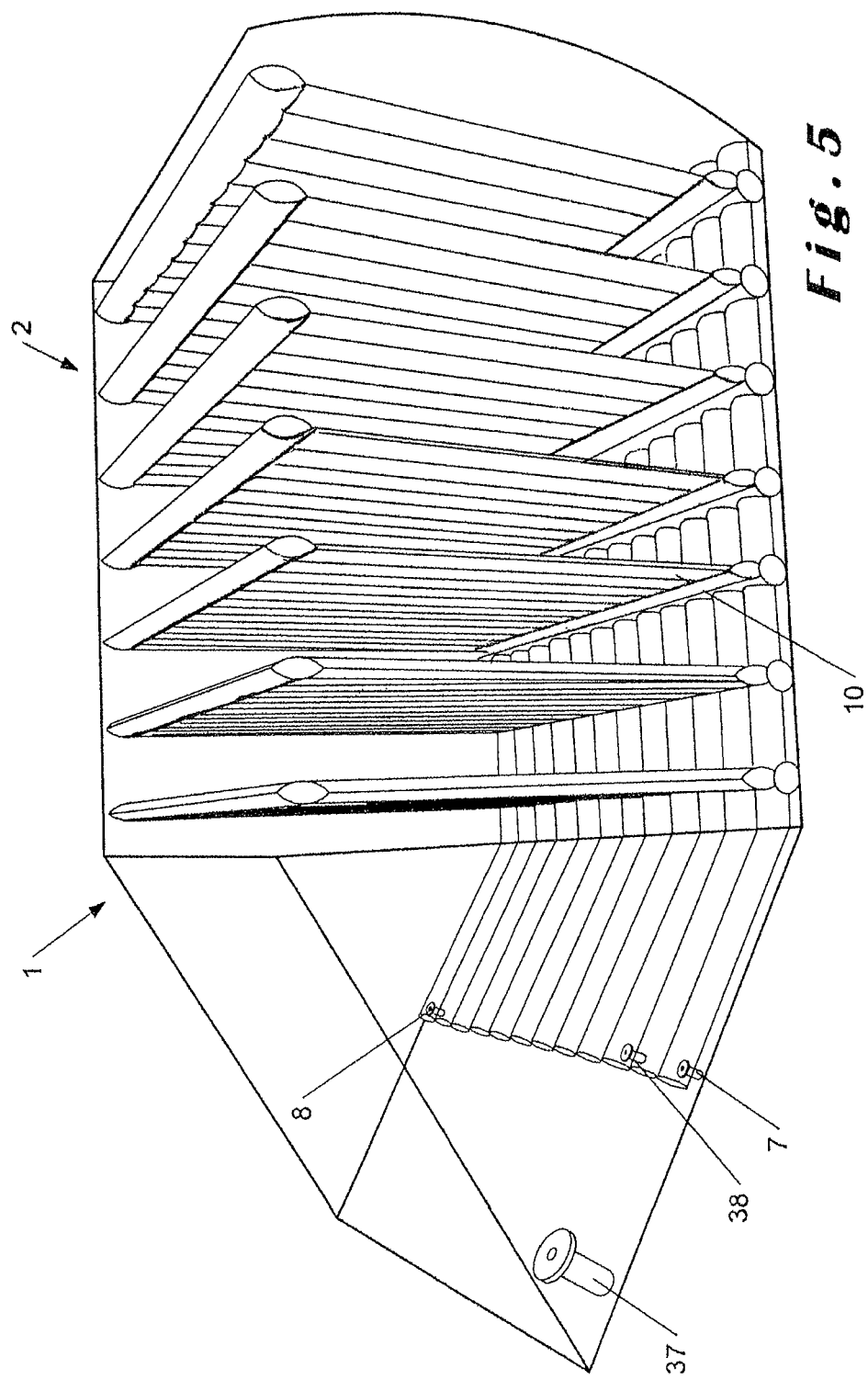
FIG. 5 shows a schematic view of another preferred embodiment of the bioreactor according to this invention.
Figure 6:
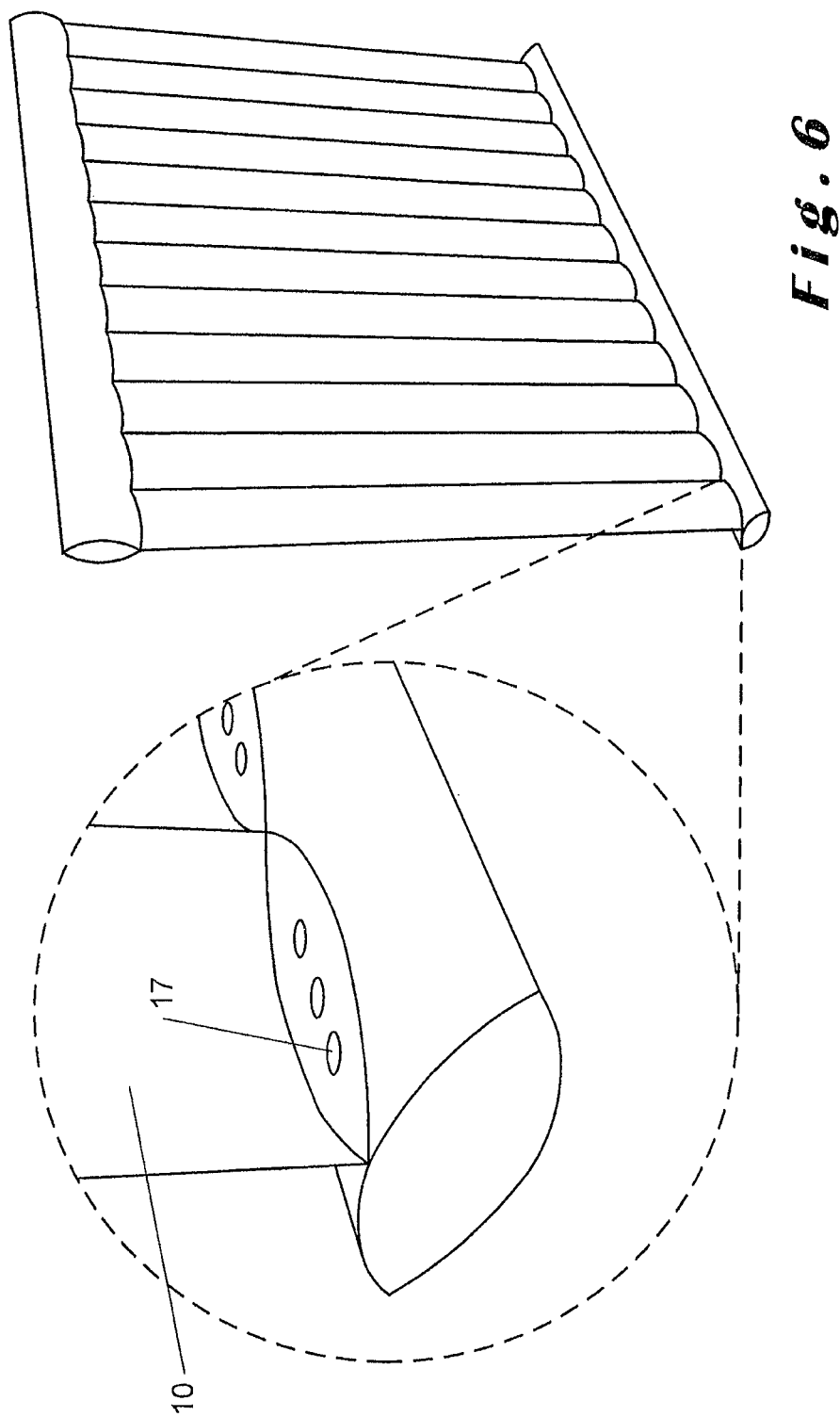
FIG. 6 shows a detail of a preferred embodiment of a chamber inlet of the at least one chamber of a bioreactor according to this invention.

Each of the chambers of the bioreactor according to this invention comprises a chamber inlet 13, 17 for supplying material to be treated to the chamber and a chamber outlet 14, 18 for discharging treated material from the chamber. The chamber inlet and outlet are preferably made in one piece with the bioreactor. The chamber inlet and outlet may take any form considered suitable by the person skilled in the art. The chamber inlet can take the form of an opening as shown in FIG. 6. Similarly, the chamber outlet can take the form of an opening. The housing of the bioreactor according to this invention comprises a housing inlet 7 connected to the chamber inlet for supplying the materials to be treated to the chamber inlet of the chambers. The housing also comprises a housing outlet 8 connected to the chamber outlet for discharging the reaction products which leave the chambers through the chamber outlets. The housing inlet and outlet are preferably made in one piece with the bioreactor as shown in FIG. 5. The housing inlet and outlet may take any form considered suitable by the person skilled in the art. The housing inlet and outlet 7, 8 can take the simple form of an opening, in which, when installing the reactor, an additional piece is placed. The housing inlet and outlet can also be made of a plastic material with a lower flexibility and higher thickness than the rest of the bioreactor, which is connected to the housing. The materials to be treated can be fluid, solid or gaseous or can contain two or more therefrom. The end products can also be fluid, solid or gaseous or two or more therefrom. The chamber and/or housing inlet is usually situated at the lower side of the bioreactor, the chamber and/or housing outlet is usually situated at an upper side of the bioreactor. The chamber and/or housing inlet and outlet can be both located at a lower side or an upper side of the bioreactor.

FIG. 8 shows a detail of a bioreactor according to this invention in which the housing outlet is located at a lower side of the bioreactor. The bioreactor as shown in FIG. 8 comprises a number of adjacent chambers. Each chamber comprises a first and second opposing chamber wall 11, 12. The first chamber wall 11 is preferably made of a first plastic foil, the second chamber wall 12 is preferably made of a second plastic foil. The first and second plastic foil are locally connected to each other. The connection is interrupted to allow a large exchange of materials between the different chambers. The bioreactor shown in FIG. 8 further comprises a housing wall to which each chamber is at least partly connected (not shown). The bioreactor shown in FIG. 8 further comprises an overflow chamber provided for receiving and discharging the treated material above a predetermined level in the at least one chamber. The overflow chamber extends parallel to the flow direction of the material through the at least one chamber and comprises a side wall of the housing and a separation wall which extends up to the predetermined level. The separation wall can be a side wall of the at least one chamber adjacent the housing or a separate wall. The overflow chamber functions as chamber outlet for the at least one chamber. In case treated material reaches the level defined by the upper side of the chamber wall of the overflow chamber, treated material is discharged from the at least one chamber to the housing outlet, which is usually provided at the bottom of the housing wall of the bioreactor. The overflow chamber may also function as an outlet for other kinds of materials, such as gases. Providing the housing outlet at the bottom side of the bioreactor has the advantage that it is easier to fabricate. Another advantage is that, in case the bioreactor is used as a photobioreactor, the housing and chamber outlet do not adversely affect the efficiency of the bioreactor because of absorption of part of the slanting light.

As shown in FIGS. 1, 2 and 4 the first and second sheet are only connected to each other along part of their height, as a result of which a supply pipe 13 is formed at the lower along the row of adjacent chambers for supplying the materials to be treated to the chambers 10, 20, and a discharge pipe 14 is formed at the top of the chambers for discharging the end product. If desired, the supply pipe 13 and/or discharge pipe 14 can extend along the whole or part of the row of adjacent chambers.

A preferred embodiment of the chamber and housing inlet is shown in FIG. 5. The bioreactor shown in FIG. 5 comprises a number of parallel extending rows of adjacent chambers. One row of adjacent chambers is formed by at least partly connecting a first and a second sheet of plastic material in height direction of the at least one chamber. The first and second sheet are only connected to each other along part of their height, as a result of which a lower and upper pipe is formed. The upper pipe may for instance be in connection with an overflow chamber in such a way that treated material is discharged from each of the chambers through the upper pipe to the overflow chamber to the housing outlet 8. The different chambers of one row are connected to each other, for instance with the aid of an interrupted connection between the different chambers. The bioreactor comprises at least one supply pipe integrated within the housing of the bioreactor and extending in longitudinal direction of the bioreactor and connecting the different parallel rows of adjacent chambers. The supply pipe is preferably made of a flexible sheet material. Preferably, at each intersection between the supply pipe and the row of chambers, a hole is made in the supply pipe, which functions as the chamber inlet for that row of adjacent chambers as shown in FIG. 6. The supply pipe may be connected to each of the chambers through the lower pipe as is shown in FIG. 5. The material to be treated is then first delivered from the supply pipe to the lower pipe, which then supplies each of the chambers with the material to be treated. The supply pipe further comprises a housing inlet, which is provided in the form of an opening in the supply pipe extending through the housing wall, in which a connector piece is inserted. Material to be treated is supplied to the housing inlet and is then transported through the supply pipe to the different chamber inlets. Because each of the chamber inlets is preferably made in one piece with the bioreactor and because each of the chamber inlets is connected to the housing inlet, it is not necessary to connected each of the chamber inlets separately to the supply pipe when setting up the bioreactor. It is sufficiently to connect the housing inlet to the supply pipe.

Figure 7:
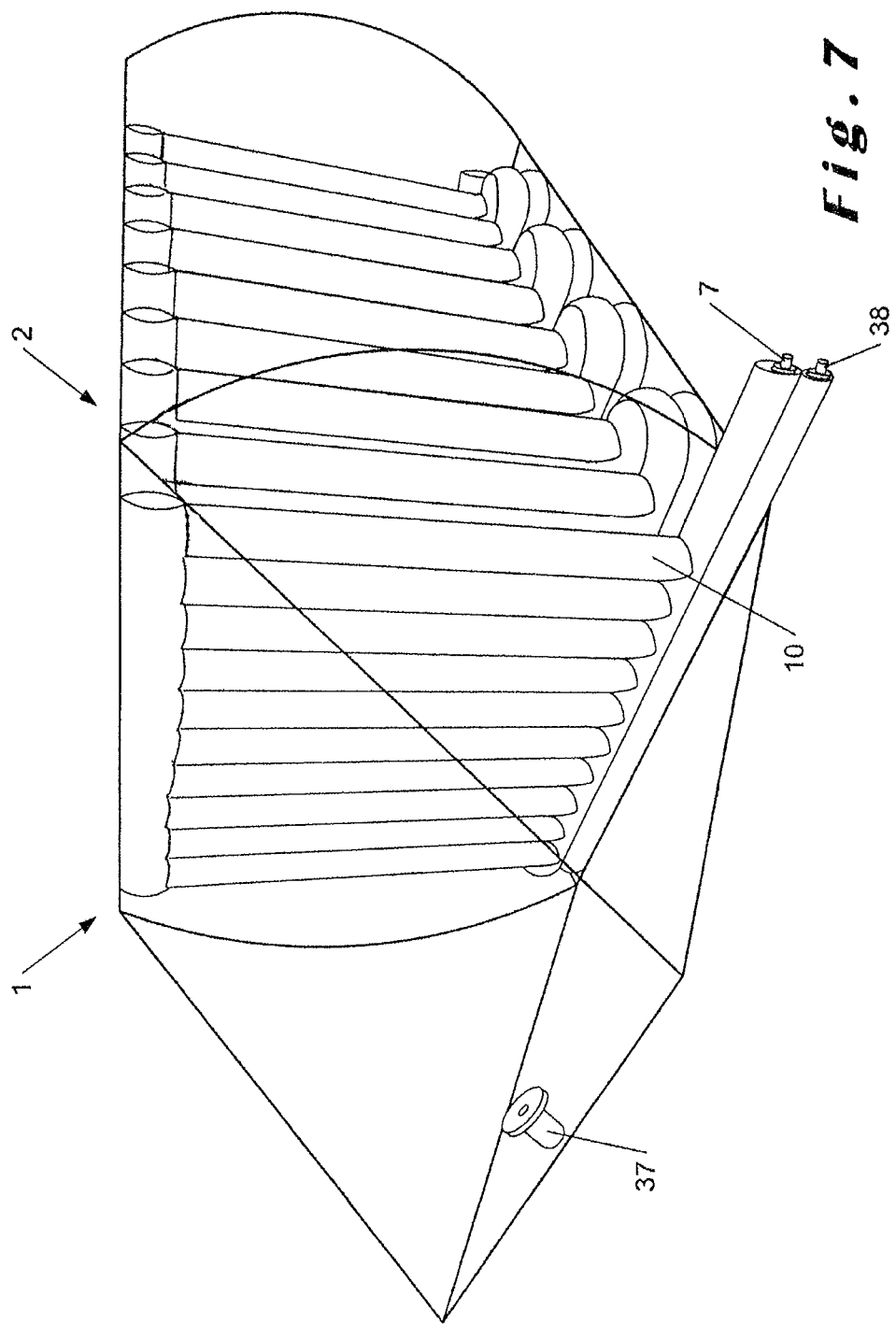
FIG. 7 shows a schematic view of another preferred embodiment of the bioreactor according to this invention.

Another preferred embodiment of the chamber and housing inlet is shown in FIG. 7. The bioreactor shown in FIG. 7 comprises a number of parallel extending rows of adjacent chambers. One row of adjacent chambers is formed by at least partly connecting a first and a second sheet of plastic material in height direction of the at least one chamber. The first and second sheet are only connected to each other along part of their height, as a result of which an upper pipe is formed. The bioreactor comprises a supply pipe integrated within the housing of the bioreactor and which is hairpin bent at a lower side of the bioreactor, in such a way that it extends beneath each row of adjacent chambers. The supply pipe comprises an amount of openings which enable it to deliver the material to be treated to each of the chambers of the bioreactor. Preferably, the supply pipe comprises an opening at each intersection with a chamber. This allows the connection between adjacent chambers to be continuous or interrupted. The supply pipe is preferably made of a flexible sheet material. The housing inlet shown in FIG. 7 is the same as the one shown in FIG. 5, but can have any other shape considered suitable by the person skilled in the art. Because each of the chamber inlets is made in one piece with the bioreactor and because each of the chamber inlets is connected to the housing inlet, it is not necessary to connected each of the chamber inlets separately to the supply pipe when setting up the bioreactor.

In order to provide each chamber with the same amount of material to be treated and/or gases, the chamber inlets are usually provided with orifices which deliver the material to be treated and/or gases under pressure to the at least one chamber. By controlling the pressure with which the material to be treated and/or gases are delivered to the at least one chamber, the bioreactor is able to deliver the same amount of material to be treated and/or gases to each of the chambers of the bioreactor, irrespective of level differences between the different chambers.

The shape of the chamber outlets and housing outlet can be the same as the chamber inlet and housing inlet, but may for instance be provided on an upper side of the bioreactor.

In case the bioreactor is used as a photobioreactor, the bioreactor preferably comprises a gas housing inlet and a gas chamber inlet to each of the chambers, for supplying a gas to each of the chambers. The gas housing inlet and chamber inlet are preferably made in one piece with the bioreactor, in such a way that, when setting up the bioreactor, there is no need to individually connect the different gas chamber inlets to the gas supply. In FIGS. 5 and 7 the bioreactor comprises a gas supply pipe, which extends parallel to the material supply pipe, and which has a similar shape as the material supply pipe. Gas may be delivered in a pulsating way to the gas housing inlet 38. This has the advantage that part of the material, which tends to adhere to the inside of a chamber wall, is loosened. This results in a reduction of lost material and an improved efficiency of the overall bioreactor.

The bioreactor according to this invention is self-supporting, which means that the bioreactor can be set up without the need for connecting or suspending the bioreactor or part of the bioreactor to a supporting structure. This self-supporting property involves that the bioreactor 1, and particularly the housing 2, forms a closed volume and that in the bioreactor a reactor pressure prevails which is higher than the external pressure outside the bioreactor. This can be achieved in a number of different ways. An increased pressure in the bioreactor can for instance be obtained by providing the chambers 10, 20 with an overpressure, by exerting for instance an overpressure on the fluid or gas in the chambers 10, 20. An increased pressure can also be obtained by means of the system shown in FIGS. 2, 5 and 7, in which the spaces 30 between the chambers are filled with a medium under increased pressure. The medium can for instance be a gas or a fluid, or a first and second fluid, the second fluid being on top of the first fluid, or a lower fluid phase and upper gas phase. In this case the housing will also comprise an inlet 37 for supplying the medium under pressure as is shown in FIGS. 5 and 7. In case the density inside the chamber is smaller than the density of the surrounding medium, it is sufficient to connect the at least one chamber with its bottom side to the housing wall. Gas bubbles delivered to the bottom side of the chamber will cause the at least one chamber with sufficient structure. The medium which is provided between the chambers may be conditioned and for instance used to improve the efficiency of the bioreactor. The conditioning of the medium between the different rows of chambers may for instance be used to reduce the risk to growth of algae at the outside of the chambers or to control the temperature inside the bioreactor. In case the medium is a liquid, the medium functions as a temperature buffer and conditions to a certain extend the temperature inside the bioreactor.

The bioreactor according to this invention has the advantage that all parts, i.e. the reactor walls and supplies—inlets and dischargers—outlets can be made of flexible sheet material. However, there is still a possibility to make the parts which form the inlet and outlet in another material, which is less flexible, but stronger and can better withstand rough treatment. In this way a system is provided which, in the uninstalled and unfilled condition, can be folded up or rolled up to a small volume and needs few space for stocking and is easy to transport. Demounting is also very simple. By adjusting the medium to the conditions, the bioreactor according to this invention is suited to be installed on a number of different places, places which are not being used useful for the moment. It is particularly advantageous that the bioreactor according to this invention does not consume water as a result of evaporation, since the bioreactor forms a closed volume. The bioreactor can for instance be installed on the land, but also in the water. In this last case, one can choose to fill the spaces 30 as a whole or partly with fluid, and let or let not float the bioreactor in the water. In case the bioreactor is installed in the water, the pressure inside the bioreactor needs to be at least higher than the pressure caused by the height of the adjacent water column in order to avoid the collapse of parts of the bioreactor.

The bioreactor according to this invention is suitable for use in a wide variety of different applications. The bioreactor is particularly suitable for use as photobioreactor, especially for growing biomass, but also as a normal bioreactor. In that case food for the biomass is supplied through the inlet 7 to the bioreactor and the bioreactor will usually comprise an additional gas inlet for supplying gas.

The bioreactor according to this invention meets the need for a bioreactor with high yield and low investment-, material- and installment costs, resulting in a system which is cost-effective.

Algae are the most efficient organisms present in nature for production of biomass. Algae are capable of producing biomass at a rate which is 10 to 30 times higher than that obtained through agriculture. This is particularly important for high populated areas such as Western Europe, where energy production from the harvesting of crops is limited by the limited amount of agricultural land. Additional, algae can produce large amounts of oil and fat acids, but can also be used for the production of special chemicals. Therefore algae are suited as a source for the oleochemistry, pharmacy, food industry. The bioreactor according to this invention can for instance by used advantageous in the production of special oils for use in the food industry, cosmetics, perfume, personal health care products, biolubricants and biofuels. Especially that last application is of importance because amounts can be produced which are several times higher than the amount obtained through the classical agriculture.

The invention claimed is:

1. A bioreactor (1) comprising a plurality of chambers (10, 20), each of the plurality of chambers comprising a chamber wall (11, 12, 15, 21, 22) and being provided for receiving biomass, each of the plurality of chambers further comprising a chamber inlet (13,17) for supplying the material to be treated to the chamber (10, 20) and a chamber outlet (14, 18) for discharging treated material from the chamber (10, 20), the plurality of chambers (10, 20) being made of a material that comprises at least one flexible film of a plastic material, wherein:
the bioreactor comprises a housing with a surrounding housing wall which forms a closed volume in which the plurality of chambers are (10, 20) is included,
the plurality of chambers (10, 20) comprises a plurality of rows (25, 31, 32) of adjacent chambers which are connected to each other,
a space (30) is provided between adjacent rows of the plurality of rows (25, 31, 32) of chambers which contains a medium under a pressure which is higher than the external pressure outside the bioreactor, but lower than the chamber pressure in each of the plurality of chambers (10, 20),
a chamber pressure prevails in each of the plurality of chambers (10, 20) which is higher than the external pressure outside the bioreactor,
at least part of the plurality of chambers (10, 20) are connected to and integrated with the housing wall (3, 4, 5, 9, 19),
the housing wall is made of a flexible plastic material,
the housing has a housing inlet (7) which is connected to the plurality of chamber inlets for supplying material to the chamber inlet (13, 17) and a housing outlet (8) which is connected to the plurality of chamber outlets for discharging treated material from the chamber outlet (14, 18),
the bioreactor a reactor pressure is maintained which is higher than an external pressure outside the bioreactor, in such a way that the bioreactor is self-supporting.

2. A bioreactor according to claim 1, characterized in that the plurality of chambers (10, 20) extends in height direction of the bioreactor.

3. A bioreactor according to claim 1, characterized in that the plurality of chamber (13, 17) and/or housing (7) inlets and chamber (14, 18) and/or housing (8) outlets are made of a flexible sheet material in one piece with the bioreactor.

4. A bioreactor according to claim 1, characterized in that each of the plurality of chambers comprises a first (11, 21) and second (12, 22) chamber wall for forming a chamber surrounding wall (15) for the chamber (10, 20), the first (11, 21) and second (12, 22) chamber wall being at least partly connected to each other in height direction of the chamber (10, 20), the first (11, 21) and second (12, 22) chamber wall being made of a flexible sheet of a plastic material.

5. A bioreactor according to claim 4, characterized in that the housing (2) comprises a housing surrounding wall (3) and in that at least one of the first (11, 21) and second (12, 22) chamber wall forms part of the housing surrounding wall (3).

6. A bioreactor according to claim 4, characterized in that the first (11, 21) and second (12, 22) chamber wall of the plurality of chambers (10, 20) respectively comprise a first (23) and second (24) upper edge and a first (26) and second (27) lower edge, the first (23) and second (24) upper edge being connected to each other and the first (26) and second (27) lower edge being connected to each other.

7. A bioreactor according to claim 4, characterized in that the housing of the bioreactor comprises an upper (4) and lower (5) housing wall, the first (11, 21) and second (12, 22) chamber wall of the plurality of chambers (10, 20) respectively comprising a first (23) and second (24) upper edge and a first (26) and second (27) lower edge and the first (23) and second (24) upper edge being connected to the upper housing wall (4) and the first (26) and second (27) lower edge being connected to the lower housing wall (5).

8. A bioreactor according to claim 1, characterized in that the connection between the adjacent chambers comprises at least one interrupted joint.

9. A bioreactor according to claim 1, characterized in that the housing comprises at least one medium inlet (37) for supplying said medium to said space.

10. A bioreactor according to claim 1, characterized in that means for providing an increased pressure are chosen from a fluid or a gas or a two- or more layer system with a lower and upper layer, the lower layer being a first fluid and the upper layer being chosen from a second fluid or a gas.

11. A bioreactor according to claim 4, characterized in that the first (11, 21) and second (12, 22) chamber wall of the plurality of chambers is made of a first material of a sheet of a material which is transparent for light and in that the housing (2) of the bioreactor is at least partly made of a second material of a light transparent foil, the first and second material being the same or different.

12. A bioreactor according to claim 1, characterized in that at least part of the housing wall comprises a light reflecting sheet material.

13. An integrated system, comprising two or more bioreactors according to claim 1, characterized in that the bioreactors are connected to each other with a connection piece.

14. A method of producing algae using the bioreactor according to claim 1, the method comprising:
supplying a feed to the housing inlet to the plurality of chambers; and discharging biomass produced by the algae through the housing outlet.

15. The method according to claim 14, further comprising selecting the feed from a material which is fluid, solid, gaseous or a material which contains two or more of those.

16. The bioreactor according to claim 4, characterized in that the housing of the bioreactor comprises an upper (4) and lower (5) housing wall, the first (11, 21) and second (12, 22) chamber wall of the plurality of chambers (10, 20) respectively comprising a first (23) and second (24) upper edge and a first (26) and second (27) lower edge and the first (26) and second (27) lower edge being connected to the lower housing wall (5).

* * * * *